US005744612A

United States Patent [19]
Koguro et al.

[11] Patent Number: 5,744,612
[45] Date of Patent: Apr. 28, 1998

[54] PROCESS FOR PREPARATION OF 5-SUBSTITUTED TETRAZOLES

[75] Inventors: Kiyoto Koguro; Toshikazu Oga; Norihito Tokunaga; Sunao Mitsui; Ryozo Orita, all of Takasago, Japan

[73] Assignee: Toyo Kasei Kogyo Company Limited, Osaka, Japan

[21] Appl. No.: 805,917

[22] Filed: Mar. 4, 1997

[30] Foreign Application Priority Data

Mar. 21, 1996 [JP] Japan .................................. 8-64900
Sep. 11, 1996 [JP] Japan ................................. 8-240713

[51] Int. Cl.$^6$ .................................................. C07D 257/04
[52] U.S. Cl. ...................... 548/250; 548/253; 548/254
[58] Field of Search ................................ 548/250, 253, 548/254

[56] References Cited

U.S. PATENT DOCUMENTS

| 2,977,372 | 3/1961 | Finnegan et al. | 260/308 |
|---|---|---|---|
| 4,791,210 | 12/1988 | Bison et al. | 548/250 |

FOREIGN PATENT DOCUMENTS

| 0 264 008 A2 | 4/1988 | European Pat. Off. |
| 0 291 969 A2 | 11/1988 | European Pat. Off. |
| 0 578 125 A1 | 1/1994 | European Pat. Off. |
| 7-2805 A | 1/1995 | Japan. |
| 7-53489 A | 2/1995 | Japan. |
| WO 94/07872 | 4/1994 | WIPO. |

OTHER PUBLICATIONS

J. Am. Chem. Soc., "An Improved Synthesis of 5–Substituted Tetrazoles", Finnegan et al., 1958, vol. 80, pp. 3908–3911.

J. Org. Chem., "Apparent Acidic Dissociation of Some 5–Aryltetrazoles", Herbst et al., 1957, vol. 22, pp. 1142–1145.

J. Org. Chem. "Three Synthetic Routes to a Sterically Hindered Tetrazole. A New One-Step Mild Conversion of an Amide into a Tetrazole", Duncia et al., 1991, vol. 56, pp. 2395–2400.

*Primary Examiner*—Joseph McKane
*Attorney, Agent, or Firm*—Kubovcik & Kubovcik

[57] ABSTRACT

The invention is directed to a process for preparing a 5-substituted tetrazole, the process comprising the step of reacting a nitrile with an inorganic azide salt in an aromatic hydrocarbon solvent in the presence of an amine salt. According to the invention, a 5-substituted tetrazole can be produced in a high yield with ease and safety using inexpensive raw materials while the reaction is easily controlled to inhibit a side reaction.

4 Claims, No Drawings

PROCESS FOR PREPARATION OF 5-SUBSTITUTED TETRAZOLES

FIELD OF THE INVENTION

The present invention relates to a process for preparing 5-substituted tetrazoles from nitriles with ease and safety at low costs, said tetrazoles being useful in the fields of pharmaceutical compositions, agricultural compositions, foaming agents, automotive inflators, etc.

The present invention also concerns with a process for preparing tetrazole derivatives which can be used as an intermediate in the preparation of conventional biphenyl tetrazole derivatives having a high antagonistic activity against angiotensin II.

Various researches have been conducted on processes for preparing tetrazoles from nitriles and azides, and many processes are known.

For example, in the synthesis of 5-phenyl-1H-tetrazole, dimethylformamide (DMF) is used as a solvent and $NH_4Cl$ as a catalyst (J. Am. Chem. Soc., 1958, 80, 3908). If $NH_4Cl$ is used as a catalyst in this process, it reacts with $NaN_3$ to give explosive $NH_4N_3$ as a sublimate attached to a condenser tube. Thus, the process involves a great risk in industrial manufacture of tetrazoles. However, if $NH_4Cl$ is not used, a tetrazole is produced in a significantly low yield. Stated more specifically, if a catalyst other than $NH_4Cl$, e.g. LiCl, is used, the yield would be reduced. Further the process requires a high reaction temperature and a prolonged reaction time as a whole.

In recent years, a process has been known for preparing a tetrazole using an amine salt as a catalyst in DMF solvent. However, if DMF is used as a solvent in the reaction, the DMF itself would decompose due to an alkali component such as an amine. Further, a step of adding water after the reaction is needed to reduce the solubility of a tetrazole in DMF. In this case, since DMF is a water-soluble solvent, unreacted substances would remain in the aqueous layer, consequently necessitating an additional step for separating and removing the unreacted substances from the tetrazole. Moreover, because DMF remains in the mother liquor after the reaction, this would pose problems in industrial manufacture, such as the recovery of organic solvent and the treatment of waste water. That is, the process is industrially markedly disadvantageous.

The reaction would proceed in the presence of a solvent such as aprotic polar solvents other than DMF, and ethers and cellosolves such as tetrahydrofuran, ethylene glycol dimethyl ether, diethylene glycol dimethyl ether, ethylene glycol monomethyl ether and ethylene glycol monoethyl ether. Yet, the reaction is industrially disadvantageous in the reaction rate, reaction ratio and treatment methods.

A process is known wherein an acid such as acetic acid is used as a catalyst and wherein $HN_3$ is generated in the presence of a solvent and is reacted with a nitrile (J. Org. Chem., 1957, 22, 1142). However, the process entails a relatively low reaction rate, a high reaction temperature, a prolonged reaction time and a low yield. Furthermore, toxic $HN_3$ is likely to escape from the reaction system. That is, this process is problematic from the viewpoint of industrial manufacture.

If DMF is used as a solvent in the preparation of a tetrazole from a nitrile having a complicated structure, the yield of the tetrazole may be pronouncedly reduced because of the reaction of the nitrile with DMF and the decomposition of DMF. In this case, a process is employable which uses an aromatic solvent or polar solvent and an organotin compound, organic silicon compound or the like as a catalyst to increase the organic properties of an azide for the facilitated production of the tetrazole (J. Org. Chem., 1991, 56, 2395). However, the organotin compound used in this process is generally of very high toxicity and the organometallic compound, which is expensive, is required in a large amount compared with the amount of the resulting tetrazole. The obtained tetrazole is often transformed to an oil in the separation from an organometallic compound. In this case, to remove the organometallic compound after conversion of the tetrazole to free form, this necessitates washing or extraction with hexane or like organic solvent, or extraction after treatment of the organometallic compound to enhance its solubility in the solvent for the extraction. Yet in most cases, an organometallic compound can not be completely separated from the tetrazole even by such treatment. In short, if an organometallic compound is used, a tetrazole would be difficult to industrially isolate. Further, from the viewpoint of industrial manufacture, if an organometallic compound is used, various problems are entailed which include requiring time for washing the equipment after the reaction, needing an organic solvent for washing and treating waste water containing the organometallic compound.

As described above, conventional processes for preparing tetrazoles raise various industrial problems. For example, if $NH_4Cl$ is used, a risk of giving a sublimate is involved. If DMF is used as a solvent, this offers problems such as the degradation of DMF, and the isolation of tetrazole from unreacted nitrile and the treatment of waste water due to the dissolution of DMF in water. Further if an acid is used as a catalyst, this raises problems of a low reaction rate and a low yield. If an organometallic compound is used to increase the yield of a tetrazole, this encounters an industrial problem on the separation of the obtained tetrazole from the orgaometallic compound.

Among known processes for preparing 1-(tetrazolylbiphenylmethyl)imidazole derivative of the formula (5) from 1-(cyanobiphenylmethyl)imidazole derivative of the formula (4), a process is known wherein a reaction is made in an aromatic hydrocarbon solvent or a polar solvent in the presence of an organotin azide (Japanese Unexamined Patent Publication No.53,489/1995).

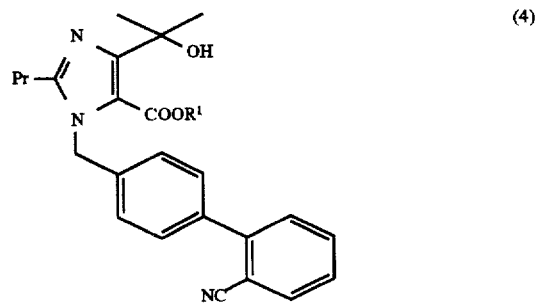

(4)

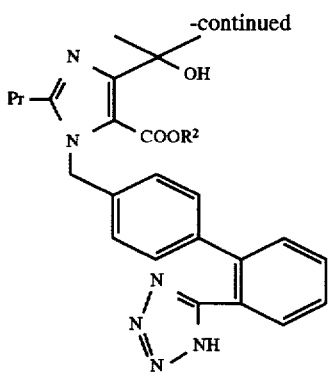
(5)

Japanese Unexamined Patent Publication No. 53,489/1995 discloses that tributyltin azide synthesized from tributyltin chloride and sodium azide is reacted with 1-(cyanobiphenylmethyl)imidazole derivative of the formula (4) in a toluene solvent, or tributyltin chloride and sodium azide are reacted with 1-(cyanobiphenylmethyl)imidazole derivative of the formula (4) in a toluene solvent after which the reaction mixture is hydrolyzed in a diluted aqueous solution of sodium hydroxide, followed by neutralization of the aqueous layer with an acid, giving 1-(tetrazolylbiphenylmethyl)imidazole derivative of the formula (5) in a yield of 54%.

However, the process presents the following problems.

(1) It is difficult to produce pure 1-(tetrazolylbiphenylmethyl)imidazole derivative because of difficulty in completely separating a tributyltin compound from 1-(tetrazolylbiphenylmethyl)imidazole derivative.

(2) The reaction product must be fully purified to remove the tributyltin compound since 1-(tetrazolylbiphenylmethyl)imidazole derivative containing even a small amount of tin can not be used as a pharmaceutical product.

(3) Generally an organotin compound is of high toxicity and calls for care in handling.

(4) Although expensive, an organotin compound is required in a large amount compared with the amount of 1-(tetrazolylbiphenylmethyl)imidazole derivative produced.

(5) For industrial manufacture, a prolonged time is taken for washing to remove the organotin compound and an organic solvent is needed for washing. In addition, a problem is posed for treating waste water containing the organotin compound.

As stated hereinbefore, conventional processes using an organotin azide pose various problems.

SUMMARY OF THE INVENTION

An object of the present invention is to provide a process capable of preparing a 5-substituted tetrazole in a high yield with ease and safety using inexpensive raw materials while the reaction is easily controlled to inhibit a side reaction.

It is another object of the invention to provide a process capable of preparing 1-(tetrazolylbiphenylmethyl)imidazole derivative of the formula (5) in a high yield with ease and safety using inexpensive raw materials without use of an organotin compound while the reaction is easily controlled to inhibit a side reaction.

The inventors of this invention carried out extensive researches on industrially advantageous processes to achieve the foregoing objects and found that an inorganic azide salt is reacted with an amine salt in the presence of an aromatic hydrocarbon as a solvent to give a hydrogen azide salt of amine which is dissolved in the aromatic hydrocarbon. Further findings were that when a hydrogen azide salt of amine is reacted with a nitrile, a tetrazole is produced with high purity in a high yield by a simple procedure and that the solvent can be re-used and the waste water can be easily treated. Based on these novel findings, the present invention was completed.

Since an inorganic azide salt is scarcely dissolved in an aromatic hydrocarbon in the synthesis of a tetrazole from an inorganic azide salt and a nitrile, a reaction has been considered not to occur in an aromatic hydrocarbon solvent. Consequently, only reactions using a polar solvent have been known.

According to the present invention, there is provided a process for preparing a 5-substituted tetrazole represented by the formula (3), the process comprising the step of reacting a nitrile represented by the formula (1) with an inorganic azide salt represented by the formula (2) in an aromatic hydrocarbon solvent in the presence of an amine salt:

RCN (1)

wherein R is an aliphatic group, an alicyclic group, an aromatic group, an aromatic aliphatic group, an aromatic alicyclic group, a heterocyclic group or a heterocyclic aliphatic group, and each group may have a substituent, $M(N_3)_n$ (2)

wherein M is an alkali metal or an alkaline earth metal, and n is 1 or 2, and

 (3)

wherein R is as defined above.

The present inventors made further investigations on industrially advantageous processes to achieve the foregoing other object and found that when an inorganic azide salt is reacted with an amine salt in an aromatic hydrocarbon as a solvent, a hydrogen azide salt of amine is produced and is dissolved in the aromatic hydrocarbon solvent. More findings were that when the hydrogen azide salt of amine is reacted with 1-(cyanobiphenylmethyl)imidazole derivative of the formula (4), optionally followed by hydrolysis of the obtained compound, 1-(tetrazolylbiphenylmethyl)imidazole derivative of the formula (5) can be produced with high purity in a high yield by a simple procedure, the solvent and the unreacted substances can be re-used, and the waste water can be easily treated. The present invention was completed based on these novel findings.

According to the present invention, there is provided a process for preparing 1-(tetrazolylbiphenylmethyl) imidazole derivative represented by the formula (5), the process comprising the step of reacting 1-(cyanobiphenylmethyl)imidazole derivative represented by the formula (4) with an inorganic azide salt represented by the formula (2) in an aromatic hydrocarbon solvent in the presence of an amine salt, optionally followed by hydrolysis of the obtained compound:

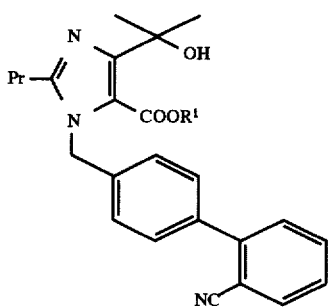

(4)

wherein R¹ is a hydrogen atom or an alkyl group having 1 to 4 carbon atoms,

M(N₃)ₙ  (2)

wherein M is an alkali metal or an alkaline earth metal, and n is 1 or 2, and

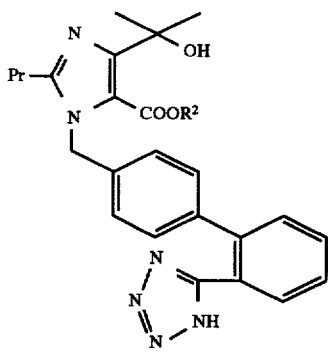

(5)

wherein R² is a hydrogen atom or an alkyl group having 1 to 4 carbon atoms.

Nitriles used as one of the raw materials in the invention include a wide range of nitriles having simple to complicated structures. In the formula (1), R means an aliphatic group, an alicyclic group, an aromatic group, an aromatic aliphatic group, an aromatic alicyclic group, a heterocyclic group or a heterocyclic aliphatic group each of which has 1 to 30 carbon atoms, and may have a substituent(s). The substituent may be a cyano group and, in this case, the nitrile of the formula (1) is a polycyano compound. Specific examples of nitriles which can be used in the invention are acetonitrile, propionitrile, butyronitrile, valeronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, hydroxypropionitrile, methoxyacetonitrile, dimethylaminopropionitrile, dimethylcyanamide, diethylcyanamide, dimethylaminoacetonitrile, cyanoacetamide, cyanoacetic acid, ethyl cyanoformate and like aliphatic nitriles; cyclopropanecarbonitrile, cyclohexanecarbonitrile, cycloheptanecarbonitrile and like alicyclic nitriles; benzonitrile, tolunitrile, cyanophenol, aminobenzonitrile, chlorobenzonitrile, bromobenzonitrile, cyanobenzoic acid, nitrobenzonitrile, anisonitrile, bromotolunitrile, methylcyanobenzoate, m-methoxybenzonitrile, aminotolunitrile, acetylbenzonitrile, naphthonitrile, biphenylcarbonitrile and like aromatic nitriles; phenylacetonitrile, phenylpropionitrile, phenylbutyronitrile, α-methylphenylacetonitrile, methylphenylacetonitrile, diphenylacetonitrile, naphthylacetonitrile, biphenylacetonitrile, aminophenylacetonitrile, nitrophenylacetonitrile, chlorobenzyl cyanide and like aromatic aliphatic nitriles; phenylcyclohexanecarbonitrile, tolylcyclohexanecarbonitrile and like aromatic alicyclic nitriles; cyanofuran, thiophenecarbonitrile, piperidinecarbonitrile, 1,5-dimethyl-2-pyrrolecarbonitrile, pyrazolecarbonitrile, cyanoindole, cyanopyridine and like heterocyclic nitriles; thiopheneacetonitrile, pyridineacetonitrile, N-(2-cyanoethyl)pyrrole, N-methyl-2-pyrroleacetonitrile, indolylacetonitrile and like heterocyclic aliphatic nitrites; cyanobiphenyl derivatives; alkoxycarbonylalkyl cyanide derivatives; and malononitrile, succinonitrile, glutaronitrile, phthalonitrile and like polycyano compounds; to which useful nitrites are not limited. Each nitrile may have a substituent(s). Preferred nitrites are, for example, acetonitrile, benzonitrile, tolunitrile, cyanophenol, aminobenzonitrile, chlorobenzonitrile, phenylacetonitrile, phenylpropionitrile, phenylbutyronitrile, diphenylacetonitrile, cyanopyridine, cyanobiphenyl derivatives, alkoxycarbonylalkyl cyanide derivatives, etc. More preferred nitrites are, for example, acetonitrile, benzonitrile, cyanobiphenyl derivatives, alkoxycarbonylalkyl cyanide derivatives, etc.

Among 1-(cyanobiphenylmethyl)imidazole derivatives of the formula (4), those wherein R¹ is an alkyl group having 1 to 4 carbon atoms are preferred and those wherein R¹ is a methyl group or an ethyl group are more preferred.

In the invention, 1-(cyanobiphenylmethyl)imidazole derivative of the formula (4) can be one prepared by any process. An example of the processes is disclosed in Japanese Unexamined Patent Publication No. 53,489/1995.

Examples of useful inorganic azide salts include azides of alkali metals or alkaline earth metals such as sodium, potassium, lithium, calcium, magnesium, etc. Azides of alkali metals are suitable and sodium azide are industrially more suitable.

The amount of the inorganic azide salt used is 1 to 5 moles, preferably 1 to 3 moles, as calculated as hydrogen azide, per mole of a nitrile of the formula (1). Desirably the inorganic azide salt is used in an equimolar amount relative to an amine salt.

The inorganic azide salt is used in an amount of 1 to 5 moles, preferably 2 to 4 moles, as calculated as hydrogen azide, per mole of 1-(cyanobiphenylmethyl)imidazole derivative of the formula (4). Desirably the inorganic azide salt is used in an equimolar amount relative to an amine salt.

Amine salts which can be used in the invention are formed from an amine and an acid. Useful amines can be any of primary, secondary and tertiary amines, and aliphatic amines are preferred. Useful amine salts include primary amine salts such as methylamine salt, ethylamine salt, propylamine salt, butylamine salt, amylamine salt, hexylamine salt, cyclohexylamine salt, heptylamine salt, octylamine salt, allylamine salt, benzylamine salt, α-phenylethylamine salt, β-phenylethylamine salt, etc.; secondary amine salts such as dimethylamine salt, diethylamine salt, dipropylamine salt, dibutylamine salt, diamylamine salt, dihexylamine salt, dicyclohexylamine salt, diallylamine salt, morpholine salt, piperidine salt, hexamethyleneimine salt, etc.; and tertiary amine salts such as trimethylamine salt, triethylamine salt, tripropylamine salt, tributylamine salt, triamylamine salt, trihexylamine salt, triallylamine salt, pyridine salt, triethanolamine salt, N-methylmorpholine salt, N,N-dimethylcyclohexylamine salt, N,N-dimethylaniline salt, N,N,N',N'-tetramethylethylenediamine salt, 4-dimethylaminopyridine salt, etc. to which useful amine salts are not limited. These amine salts can be used either alone or in combination.

Acids to be used for forming such salt are basically those which, together with an amine, are capable of producing a salt. Useful acids include, for example, inorganic acids such as hydrochloric acid, hydrogen bromide, sulfuric acid, nitric acid, phosphoric acid, boric acid, hydrogen azide, chloric acid, carboxylic acid, hydrogen sulfide and the like; and organic acids such as formic acid, acetic acid, trifluoroacetic acid, propionic acid, oxalic acid, methanesulfonic acid, benzenesulfonic acid, toluenesulfonic acid and the like to which useful acids are not limited. Preferred acids are, for example, hydrochloric acid, hydrogen bromide, sulfuric acid, hydrogen azide, acetic acid, trifluoroacetic acid, etc.

Preferred amine salts include, for example, triethylamine hydrochloride.

Useful amine salts include commercially available products, and the salt synthesized in the reaction system by the reaction of an amine with an acid.

The amount of the amine salt used is sufficient if it is a minimum amount required for the progress of the reaction. The amount is 1 to 5 moles, preferably 1 to 3 moles, as calculated as an amine, per mole of a nitrile of the formula (1). The molar ratio of the amine salt affects the reaction rate and yield. Especially it is preferred to use the amine salt in an equimolar amount relative to the inorganic azide salt.

With respect to 1-(cyanobiphenylmethyl)imidazole derivative of the formula (4), the amine salt is used in an amount of 1 to 5 moles, preferably 2 to 4 moles, as calculated as an amine, per mole of the derivative. The molar ratio of the amine salt affects the reaction rate and yield. Especially it is preferred to use the amine salt in an equimolar amount relative to the inorganic azide salt.

Solvents preferred in the reaction include aromatic hydrocarbons inert to the reaction. Aromatic hydrocarbons which are industrially suitable and proper for the reaction are, for example, benzene, toluene, xylene, mesitylene, ethylbenzene, chlorobenzene, nitrobenzene, cumene, chlorotoluene, etc. among which toluene and xylene are preferred. A mixture of at least two of these aromatic hydrocarbons can be used in the reaction. The amount of the aromatic hydrocarbon used may be a minimum amount which allows the reaction to proceed. The amount is usually 1 to 100 ml, preferably 2 to 50 ml, per gram of the nitrile of the formula (1) or gram of 1-(cyanobiphenylmethyl) imidazole derivative of the formula (4). The solvent may contain about 5% or less of water.

The reaction temperature is not specifically limited, but can be selected from a wide range of 20° to 150° C., preferably 70° to 140° C. although depending on a combination of starting materials, i.e. nitrile, amine salt and solvent. The reaction time is not critical but usually in the range of 1 to 120 hours, preferably 3 to 50 hours.

The reaction of the present invention proceeds at a high rate, giving only a small amount of by-products. That is, the reaction ensures a high efficiency and can produce the desired product in a higher yield than conventional techniques.

When water is added after the reaction, a 5-substituted tetrazole is present as an amine salt in an aqueous layer. The layer of the aromatic hydrocarbon solvent can be removed by fractionation. When the reaction is terminated leaving an unreacted nitrile portion as dissolved in the aromatic hydrocarbon, the portion can be removed and recovered together with the aromatic hydrocarbon solvent by fractionation. The aromatic hydrocarbon solvent can be easily recovered by distillation and can be re-used. When recovered merely by fractionation, the aromatic hydrocarbon solvent even containing a small amount of water and the unreacted nitrile fraction can be re-used by itself in the reaction.

After fractionation, an acid is added to the aqueous layer containing the amine salt of a 5-substituted tetrazole to give a 5-substituted tetrazole in free form. In this case, the amine forms a salt, along with the added acid, and the salt is dissolved in water. If the obtained 5-substituted tetrazole in free form is soluble in water, an additional step is necessary for separating the 5-substituted tetrazole in free form from the amine salt (e.g. by extracting the 5-substituted tetrazole in free form with a suitable solvent and distilling off the solvent). On the other hand, if insoluble in water, the 5-substituted tetrazole in free form is filtered and isolated as such, giving a substantially pure 5-substituted tetrazole. Consequently the invention has one of the features in that as described above, the procedure is very easy and that a 5-substituted tetrazole can be safely isolated.

When the group represented by R in the formula (3) has a hydrolyzable group, the hydrolyzable group may be converted to a different group on hydrolysis in the post-treatment after the reaction.

Even when a nitrile having a complicated structure is used, the reaction of the invention easily proceeds without use of an organometallic compound. Because of the absence of an organometallic compound, the post-treatment after the reaction is easy and inexpensive.

The process of the invention is improved over techniques using an organometallic compound in safety, toxicity, handleability, costs, ease of procedure, reaction time, yield, etc.

Especially when using, as the raw material, 1-(cyanobiphenylmethyl)imidazole derivative of the formula (4) wherein $R^1$ is an alkyl group, the ester moiety may be hydrolyzed with a hydroxide of alkali metal or alkaline earth metal and water after the reaction. Examples of useful hydroxides of alkali metals are lithium hydroxide, sodium hydroxide, potassium hydroxide, etc. Among them, sodium hydroxide is preferred. Useful hydroxides of alkaline earth metals are, for example, barium hydroxide and calcium hydroxide among which calcium hydroxide is favorable. The reaction temperature in the hydrolysis is not critical, but preferably 10° to 40° C. The reaction time in the hydrolysis is not critical but preferably 1 to 5 hours.

After completion of the hydrolysis, the aqueous layer is washed with an organic solvent such as an aromatic hydrocarbon and the pH is adjusted to an acidity range, whereby 1-(tetrazolylbiphenylmethyl) imidazole derivative of the formula (5) wherein $R^2$ is a hydrogen atom can be precipitated. The obtained 1-(tetrazolylbiphenylmethyl)imidazole derivative can be washed with an alcohol, when so required.

After the reaction, unreacted 1-(cyanobiphenylmethyl) imidazole derivative of the formula (4) remains as dissolved in the aromatic hydrocarbon solvent. The remaining derivative can be removed and recovered, along with the aromatic hydrocarbon solvent, by fractionation. The aromatic hydrocarbon solvent can be easily recovered by distillation and can be re-used.

Since an organotin compound is not used in the invention, a tin can not be present in 1-(tetrazolylbiphenylmethyl) imidazole derivative of the formula (5). Accordingly post-treatment and purification are easy and high-quality 1-(tetrazolylbiphenylmethyl)imidazole derivative can be easily produced in the invention. One feature of the present invention resides in that the procedure is easy and 1-(tetrazolylbiphenylmethyl)imidazole derivative of the formula (5) can be safely isolated at low costs.

Consequently, the process of the present invention is outstanding in safety, toxicity, handleability, costs, ease of procedure, yield, etc. as compared with processes using an organotin compound.

As described above, this invention is directed to an pronouncedly advantageous process for preparing a 5-substituted tetrazole on an industrial scale.

Further, the invention provides a significantly advantageous process for preparing 1-(tetrazolylbiphenylmethyl) imidazole derivative of the formula (5) on an industrial scale.

According to the present invention, a 5-substituted tetrazole of the formula (3) can be easily and safely prepared from inexpensive raw materials in a high yield while the reaction is easily controlled to inhibit a side reaction.

Moreover, in accordance with the present invention, 1-(tetrazolylbiphenylmethyl)imidazole derivative of the formula (5) can be easily and safely prepared from inexpensive raw materials in a high yield without use of an organotin compound while the reaction is easily controlled to inhibit a side reaction.

BEST MODE FOR CARRYING OUT THE INVENTION

The present invention is described below in more detail with reference to the following Examples. The reaction conditions in Examples are tabulated in Tables 1 to 6. The present invention, however, is not limited to the Examples.

EXAMPLE 1

Into a 200-ml flask equipped with a reflux condenser, thermometer and stirrer were placed 5.16 g (0.050 mole) of benzonitrile, 4.23 g (0.065 mole) of sodium azide, 8.95 g (0.065 mole) of triethylamine hydrochloride and 52 ml of toluene. The mixture was heated with stirring to a temperature of 95° to 100° C. to undergo a reaction for 7 hours. After completion of the reaction, the reaction mixture was cooled to room temperature and 104 ml of water was added for fractionation. To the aqueous layer was added 6.57 g (0.065 mole) of 36 wt % hydrochloric acid, thereby precipitating 5-phenyl-1H-tetrazole. The precipitate was filtered and dried, giving 7.02 g (0.048 mole) of 5-phenyl-1H-tetrazole (yield 96.0% based on benzonitrile).

EXAMPLE 2

A reaction was conducted for 7 hours by following the same procedure as in Example 1 with the exception of using 5.86 g (0.050 mole) of metatolunitrile in place of benzonitrile, whereby 7.46 g (0.047 mole) of 5-(3-methylphenyl)-1H-tetrazole was produced (yield 93.2% based on metatolunitrile).

EXAMPLE 3

A reaction was conducted for 24 hours by following the same procedure as in Example 1 with the exception of using 5.86 g (0.050 mole) of orthotolunitrile in place of benzonitrile, whereby 5.05 g (0.032 mole) of 5-(2-methylphenyl)-1H-tetrazole was produced (yield 63.1% based on orthotolunitrile).

EXAMPLE 4

A reaction was conducted for 7 hours by following the same procedure as in Example 1 with the exception of using 5.86 g (0.050 mole) of paratolunitrile in place of benzonitrile, whereby 7.73 g (0.048 mole) of 5-(4-methylphenyl)-1H-tetrazole was produced (yield 96.5% based on paratolunitrile).

EXAMPLE 5

Into the same device as used in Example 1 were placed 5.96 g (0.050 mole) of orthocyanophenol, 9.76 g (0.150 mole) of sodium azide, 20.65 g (0.150 mole) of triethylamine hydrochloride and 60 ml of toluene. The mixture was reacted for 5 hours in the same manner as in Example 1, giving 7.95 g (0.049 mole) of 5-(2-hydroxyphenyl)-1H-tetrazole (yield 98.0% based on orthocyanophenol).

EXAMPLE 6

Into the same device as used in Example 1 were placed 1.19 g (0.010 mole) of paracyanophenol, 1.95 g (0.030 mole) of sodium azide, 4.13 g (0.030 mole) of triethylamine hydrochloride and 12 ml of toluene. The mixture was reacted for 8 hours in the same manner as in Example 1, giving 1.34 g (0.0083 mole) of 5-(4-hydroxyphenyl)-1H-tetrazole (yield 82.7% based on paracyanophenol).

EXAMPLE 7

A reaction was conducted for 1 hour by following the same procedure as in Example 1 with the exception of using 5.86 g (0.050 mole) of phenylacetonitrile in place of benzonitrile and 59 ml of toluene, whereby 5.66 g (0.035 mole) of 5-benzyl-1H-tetrazole was produced (yield 70.7% based on phenylacetonitrile).

EXAMPLE 8

A reaction was conducted for 5 hours by following the same procedure as in Example 1 with the exception of using 6.56 g (0.050 mole) of 3-phenylpropionitrile in place of benzonitrile and 66 ml of toluene, whereby 8.16 g (0.047 mole) of 5-phenethyl-1H-tetrazole was produced (yield 93.7% based on 3-phenylpropionitrile).

EXAMPLE 9

A reaction was conducted for 7 hours by following the same procedure as in Example 1 with the exception of using 7.26 g (0.050 mole) of 4-phenylbutyronitrile in place of benzonitrile and 73 ml of toluene. After completion of the reaction, the reaction mixture was cooled to room temperature and 74 ml of water was added for fractionation. To the aqueous layer was added 15.22 g (0.030 mole) of 36 wt % hydrochloric acid, and 5-phenylpropyl-1H-tetrazole was extracted with ethyl acetate. The ethyl acetate layer was washed with a 10 wt % aqueous solution of sodium chloride, dried over magnesium sulfate, filtered, and distilled to remove ethyl acetate. This procedure gave 8.03 g (0.043 mole) of 5-phenylpropyl-1H-tetrazole (yield 85.3% based on 4-phenylbutyronitrile).

EXAMPLE 10

A reaction was conducted for 23 hours by following the same procedure as in Example 1 with the exception of using 5.91 g (0.050 mole) of 2-aminobenzonitrile in place of benzonitrile, whereby 7.32 g (0.045 mole) of 5-(2-aminophenyl)-1H-tetrazole was produced (yield 90.8% based on 2-aminobenzonitrile).

EXAMPLE 11

A reaction was conducted for 28 hours by following the same procedure as in Example 1 with the exception of using 5.91 g (0.050 mole) of 3-aminobenzonitrile in place of benzonitrile, whereby 7.63 g (0.047 mole) of 5-(3-aminophenyl)-1H-tetrazole was produced (yield 94.7% based on 3-aminobenzonitrile).

EXAMPLE 12

Into the same device as used in Example 1 were placed 6.58 g (0.065 mole) of triethylamine and 52 ml of toluene.

To the mixture were added 3.19 g (0.033 mole) of concentrated sulfuric acid with stirring. Further added were 5.16 g (0.050 mole) of benzonitrile and 4.23 g (0.065 mole) of sodium azide. The mixture was heated to a temperature from 95° to 100° C. to undergo a reaction for 7 hours. The same subsequent treatment as in Example 1 was conducted, giving 7.11 g (0.049 mole) of 5-phenyl-1H-tetrazole (yield 97.3% based on benzonitrile).

EXAMPLE 13

A reaction was conducted for 8 hours by following the same procedure as in Example 12 with the exception of using 3.91 g (0.065 mole) of glacial acetic acid in place of concentrated sulfuric acid, whereby 6.17 g (0.042 mole) of 5-phenyl-1H-tetrazole was produced (yield 84.4% based on benzonitrile).

EXAMPLE 14

Into the same device as used in Example 1 were placed 5.16 g (0.050 mole) of benzonitrile, 4.23 g (0.065 mole) of sodium azide, 7.13 g (0.065 mole) of diethylamine hydrochloride and 52 ml of toluene. The mixture was reacted for 8 hours in the same manner as in Example 1, giving 7.02 g (0.048 mole) of 5-phenyl-1H-tetrazole (yield 96.0% based on benzonitrile).

EXAMPLE 15

A reaction was conducted for 8 hours by following the same procedure as in Example 14 with the exception of using 5.30 g (0.065 mole) of ethylamine hydrochloride in place of diethylamine hydrochloride, whereby 4.10 g (0.028 mole) of 5-phenyl-1H-tetrazole was produced (yield 56.1% based on benzonitrile).

EXAMPLE 16

Into the same device as used in Example 1 were placed 5.16 g (0.050 mole) of benzonitrile, 4.23 g (0.065 mole) of sodium azide, 8.95 g (0.065 mole) of triethylamine hydrochloride, 52 ml of toluene and 2.6 g of water. The mixture was reacted at a temperature of 85° to 95° C. for 8 hours, giving 6.12 g (0.042 mole) of 5-phenyl-1H-tetrazole (yield 83.7% based on benzonitrile).

EXAMPLE 17

A reaction was conducted at 76° to 79° C. for 8 hours by following the same procedure as in Example 1 with the exception of using 52 ml of benzene in place of toluene, whereby 6.67 g (0.046 mole) of 5-phenyl-1H-tetrazole was produced (yield 91.2% based on benzonitrile).

EXAMPLE 18

A reaction was conducted at a temperature of 100° to 107° C. for 5 hours by following the same procedure as in Example 1 with the exception of using 52 ml of xylene in place of toluene, whereby 7.22 g (0.049 mole) of 5-phenyl-1H-tetrazole was produced (yield 98.8% based on benzonitrile).

EXAMPLE 19

A reaction was conducted at a temperature of 100° to 102° C. for 8 hours by following the same procedure as in Example 1 with the exception of using 52 ml of nitrobenzene in place of toluene, whereby 7.19 g (0.049 mole) of 5-phenyl-1H-tetrazole was produced (yield 98.4% based on benzonitrile).

Tables 1 to 6 show Examples wherein various types of solvents were used in varied amounts, and various types of inorganic azide salts and amine salts were used in varied amounts.

Table 1 shows Examples wherein reactions were made using various types of nitrites under varied reaction conditions (reaction temperature and reaction time), while using about 10 ml of toluene per gram of a nitrile, and sodium azide and triethylamine hydrochloride respectively in an amount of 1.3 moles per mole of a nitrile (in Example 20, a reaction was performed in the same manner as in Examples 1 to 4, 10 and 11 except that the type of nitrites and reaction conditions were employed as shown in Table 1).

TABLE 1

| Ex. No. | Nitrile | Reaction Conditions | Yield (%) |
| --- | --- | --- | --- |
| 1 | phenyl-CN | 95 ~ 100° C. × 7 hr | 96.0 |
| 3 | 2-methylphenyl-CN | 95 ~ 100° C. × 24 hr | 63.1 |
| 2 | 3-methylphenyl-CN | 95 ~ 100° C. × 7 hr | 93.2 |
| 4 | 4-methylphenyl-CN | 95 ~ 100° C. × 7 hr | 96.5 |
| 10 | 2-aminophenyl-CN | 95 ~ 100° C. × 23 hr | 90.8 |
| 11 | 3-aminophenyl-CN | 95 ~ 100° C. × 28 hr | 94.7 |
| 20 | 4-aminophenyl-CN | 95 ~ 100° C. × 23 hr | 92.2 |

Table 2 shows Examples wherein reactions were made using about 10 ml of toluene per gram of a nitrile, and sodium azide and triethylamine hydrochloride respectively in an amount of 3.0 moles per mole of a nitrile, and employing various types of nitrites under varied reaction conditions (in Examples 21 to 25, reactions were conducted in the same manner as in Examples 5 and 6 with the exception of using various types of nitrites and reaction conditions as shown in Table 2).

TABLE 2

| Ex. No. | Nitrile | Reaction Conditions | Yield (%) |
|---|---|---|---|
| 5 | 2-hydroxybenzonitrile (CN, OH) | 95 ~ 100° C. × 5 hr | 98.0 |
| 6 | 4-hydroxybenzonitrile (HO-C6H4-CN) | 95 ~ 100° C. × 8 hr | 82.7 |
| 21 | 2-chlorobenzonitrile (CN, Cl) | 95 ~ 100° C. × 7 hr | 68.9 |
| 22 | 3-chlorobenzonitrile (Cl, CN) | 95 ~ 100° C. × 7 hr | 100 |
| 23 | 4-chlorobenzonitrile (Cl-C6H4-CN) | 95 ~ 100° C. × 7 hr | 99.9 |
| 24 | 1,3-dicyanobenzene (NC, CN) | 95 ~ 100° C. × 7 hr | 96.9 |
| 25 | 1,4-dicyanobenzene (NC-C6H4-CN) | 95 ~ 100° C. × 7 hr | 100 |

Table 3 shows Examples wherein reactions were made using various types of nitriles under varied reaction conditions, while employing about 10 to about 40 ml of toluene per gram of a nitrile, and sodium azide and triethylamine hydrochloride respectively in an amount of 3.0 moles per mole of a nitrile (in Examples 26 to 30, reactions were made in the same manner as in Examples 7 to 9 except that the type of nitrites and reaction conditions were varied as shown in Table 3 and the amount of toluene solvent was varied).

TABLE 3

| Ex. No. | Nitrile | Reaction Conditions | Yield (%) |
|---|---|---|---|
| 26 | $CH_3CN$ | 95 ~ 100° C. × 25 hr | 90.0 |
| 7 | $C_6H_5\text{-}CH_2CN$ | 95 ~ 100° C. × 1 hr | 70.7 |
| 8 | $C_6H_5\text{-}CH_2CH_2CN$ | 95 ~ 100° C. × 7 hr | 93.7 |
| 9 | $C_6H_5\text{-}CH_2CH_2CH_2CN$ | 95 ~ 100° C. × 7 hr | 85.3 |

TABLE 3-continued

| Ex. No. | Nitrile | Reaction Conditions | Yield (%) |
|---|---|---|---|
| 27 | diphenylacetonitrile ((C6H5)2CHCN) | 95 ~ 100° C. × 7 hr | 47.6 |
| 28 | 2-cyanopyridine | 95 ~ 100° C. × 7 hr | 100 |
| 29 | 3-cyanopyridine | 95 ~ 100° C. × 7 hr | 100 |
| 30 | 4-cyanopyridine | 95 ~ 100° C. × 7 hr | 100 |

Table 4 shows Examples wherein reactions were made using various types of solvents under varied reaction conditions, while employing about 10 ml of a solvent per gram of benzonitrile, and sodium azide and triethylamine hydrochloride respectively in an amount of 1.3 moles per mole of benzonitrile. "P5T" is an abbreviation for 5-phenyl-1H-tetrazole (same hereinafter).

TABLE 4

| Ex. No. | Solvent | Reaction conditions | P5T yield (%) |
|---|---|---|---|
| 17 | Benzene | 76–79° C. × 8 hr | 91.2 |
| 1 | Toluene | 95–100° C. × 7 hr | 96.0 |
| 18 | Xylene | 100–107° C. × 5 hr | 98.8 |
| 19 | Nitrobenzene | 100–102° C. × 8 hr | 98.4 |
| 16 | Toluene + 5% water (w/v) | 85–95° C. × 8 hr | 83.7 |

Table 5 shows Examples wherein reactions were made using different types of catalysts under different reaction conditions, while using about 10 ml of toluene per gram of benzonitrile, and sodium azide and amine salt (catalyst) respectively in an amount of 1.3 moles per mole of benzonitrile.

TABLE 5

| Ex. No. | Catalyst | Reaction conditions | P5T yield (%) |
|---|---|---|---|
| 1 | $Et_3N\cdot HCl$ | 95–100° C. × 7 hr | 96.0 |
| 14 | $Et_2NH\cdot HCl$ | 95–100° C. × 8 hr | 96.0 |
| 15 | $EtNH_2\cdot HCl$ | 95–100° C. × 8 hr | 56.1 |

Table 6 shows Examples wherein reactions were made using various types of acids to form an amine salt under varied reaction conditions, while using about 10 ml of toluene per gram of benzonitrile, and sodium azide and triethylamine respectively in an amount of 1.3 moles per mole of benzonitrile. The molar ratio of the acid is relative to benzonitrile. In Example 1, triethylamine hydrochloride was used, but the acid component is indicated in Table 6.

TABLE 6

| Ex. No. | Acid (molar ratio) | Reaction conditions | P5T yield (%) |
|---|---|---|---|
| 1 | Hydrochloric acid (1.3) | 95–100° C. × 7 hr | 96.0 |
| 12 | Sulfuric acid (0.66) | 95–100° C. × 7 hr | 97.3 |
| 13 | Acetic acid (1.3) | 95–100° C. × 8 hr | 84.4 |

EXAMPLE 31

Into the same device as used in Example 1 were placed 9.66 g (0.050 mole) of 4'-methylbiphenyl-2-carbonitrile, 6.50 g (0.100 mole) of sodium azide, 13.77 g (0.100 mole) of triethylamine hydrochloride and 96.6 ml of toluene. The mixture was reacted for 48 hours in the same manner as in Example 1, giving 10.85 g (0.046 mole) of 5-(4'-methylbiphenyl-2-yl)-1H-tetrazole (yield 91.9% based on 4'-methylbiphenyl-2-carbonitrile). The reaction is illustrated below with chemical formulas:

EXAMPLE 32

Into the same device as used in Example 1 were placed 77.3 g (0.28 mole) of methyl (2S)-2-benzyloxycarbonylamino-4-cyanobutyrate, 27.3 g (0.42 mole) of sodium azide, 57.7 g (0.42 mole) of triethylamine hydrochloride and 280 ml of toluene. Thereafter, the mixture was heated to a temperature of 82° to 83° C. to undergo a reaction for 24 hours. Subsequently the same procedure as in Example 1 was repeated, and crystals were collected by filtration. Further, the crystals were recrystallized from methanol and water, filtered and dried, giving 67.7 g (0.21 mole) of methyl (2S)-2-benzyloxycarbonylamino-4-(tetrazole-5-yl)butyrate (yield 75.8% based on methyl (2S)-2-benzyloxycarbonylamino-4-cyanobutyrate). The reaction is illustrated below with chemical formulas:

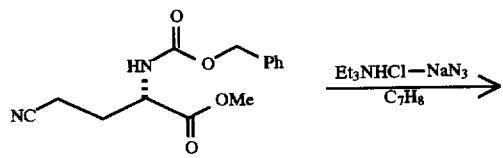

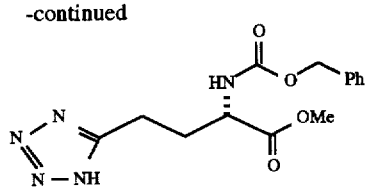

EXAMPLE 33

Into a 500-ml flask equipped with a reflux condenser, thermometer and stirrer were placed 43.5 g (0.10 mole) of ethyl ester of 1-(2'-cyanobiphenyl-4-yl)methyl-4-(1-hydroxy-1-methylethyl)-2-propylimidazole-5-carboxylic acid, 19.5 g (0.30 mole) of sodium azide, 41.3 g (0.30 mole) of triethylamine hydrochloride and 206 ml of toluene. The mixture was heated with stirring to a temperature of 95° to 100° C. to undergo a reaction for 24 hours. After completion of the reaction, the reaction mixture was cooled to room temperature. Then, the reaction mixture was analyzed by high-performance liquid chromatography and identified as ethyl ester of 4-(1-hydroxy-1-methylethyl)-2-propyl-1-{4-[2-(tetrazole-5-yl)phenyl]phenyl}methylimidazole-5-carboxylic acid (reaction ratio 87%). The reaction is illustrated below with chemical formulas:

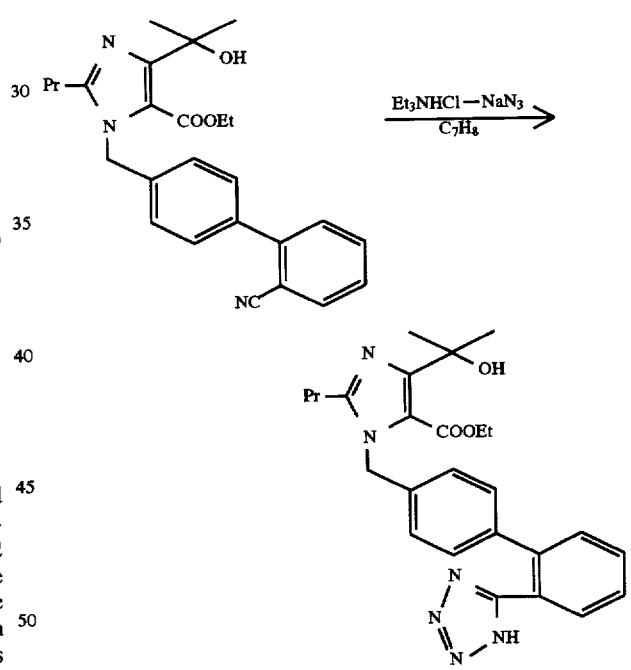

EXAMPLE 34

Into a 500-ml flask equipped with a reflux condenser, thermometer and stirrer were placed 43.5 g (0.10 mole) of ethyl ester of 1-(2'-cyanobiphenyl-4-yl)methyl-4-(1-hydroxy-1-methylethyl)-2-propylimidazole-5-carboxylic acid, 19.5 g (0.30 mole) of sodium azide, 41.3 g (0.30 mole) of triethylamine hydrochloride and 206 ml of toluene. The mixture was heated with stirring to a temperature of 95° to 100° C. to undergo a reaction for 24 hours. After completion of the reaction, the reaction mixture was cooled to room temperature. Then, 35.0 g (0.42 mole) of a 48 wt % aqueous solution of NaOH and 335 ml of water were added. The mixture was fractionated after 2 hours' stirring at room temperature. The aqueous layer was washed and fractionated with the addition of 103 ml of toluene. The aqueous layer was adjusted to a pH of 2 to 3.5 with 36 wt % hydrochloric acid to separate out crystals, which were collected by filtration and dried. The crystals were heated, washed with methanol with stirring, cooled, filtered for collection and dried, giving 32.6 g (0.07 mole) of 4-(1-hydroxy-1-methylethyl)-2-propyl-1-{4-[2-(tetrazole-5-yl)phenyl]phenyl}methylimidazole-5-carboxylic acid (yield 72.4% based on ethyl ester of 1-(2'-cyanobiphenyl-4-yl)methyl-4-(1-hydroxy-1-methylethyl)-2-propylimidazole-5-carboxylic acid). The reaction is illustrated below with chemical formulas.

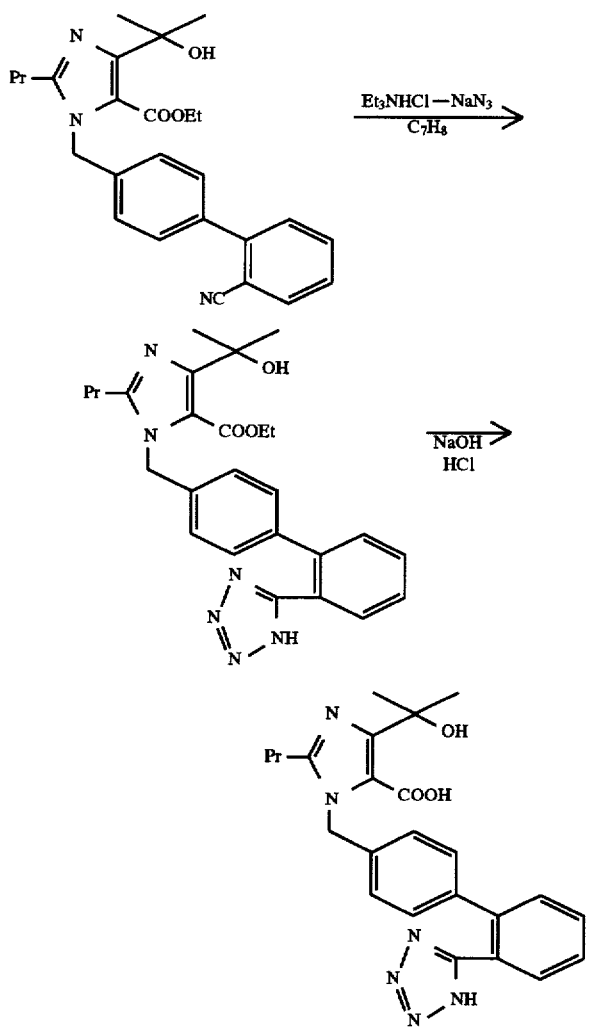

EXAMPLE 35

Into the same device as used in Example 34 were placed 43.5 g (0.10 mole) of ethyl ester of 1-(2'-cyanobiphenyl-4-yl)methyl-4-(1-hydroxy-1-methylethyl)-2-propylimidazole-5-carboxylic acid, 13.1 g (0.20 mole) of sodium azide, 31.9 g (0.23 mole) of triethylamine hydrochloride and 206 ml of toluene. Thereafter, the mixture was reacted and treated in the same manner as in Example 34, giving 27.0 g (0.06 mole) of 4-(1-hydroxy-1-methylethyl)-2-propyl-1-{4-[2-(tetrazole-5-yl)phenyl]phenyl}methylimidazole-5-carboxylic acid (yield 60.0% based on ethyl ester of 1-(2'-cyanobiphenyl-4-yl)methyl-4-(1-hydroxy-1-methylethyl)-2-propylimidazole-5-carboxylic acid).

EXAMPLE 36

Into the same device as used in Example 34 were placed 43.5 g (0.10 mole) of ethyl ester of 1-(2'-cyanobiphenyl-4-yl)methyl-4-(1-hydroxy-1-methylethyl)-2-propylimidazole-5-carboxylic acid, 8.5 g (0.13 mole) of sodium azide, 20.8 g (0.15 mole) of triethylamine hydrochloride and 206 ml of toluene. The mixture was reacted and treated in the same manner as in Example 34, giving 20.3 g (0.045 mole) of 4-(1-hydroxy-1-methylethyl)-2-propyl-1-{4-[2-(tetrazole-5-yl)phenyl]phenyl}methylimidazole-5-carboxylic acid (yield 45.0% based on ethyl ester of 1-(2'-cyanobiphenyl-4-yl)methyl-4-(1-hydroxy-1-methylethyl)-2-propylimidazole-5-carboxylic acid).

We claim:

1. A process for preparing a 5-substituted tetrazole represented by the formula (3), the process comprising the step of reacting a nitrile represented by the formula (1) with an inorganic azide salt represented by the formula (2) in an aromatic hydrocarbon solvent in the presence of an amine salt:

wherein R is an aliphatic group, an alicyclic group, an aromatic group, an aromatic aliphatic group, an aromatic alicyclic group, a heterocyclic group or a heterocyclic aliphatic group, each group having up to 30 carbon atoms and being unsubstituted or substituted with up to two substituents selected from chloro, bromo, hydroxy, methoxy, amino, carboxy, nitro, acetyl, methyl, alkoxycarbonyl and cyano,

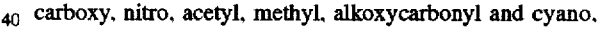

wherein M is an alkali metal or an alkaline earth metal, and n is 1 or 2, and

where R is as defined above.

2. The process according to claim 1, wherein the inorganic azide salt is sodium azide.

3. The process according to claim 1, wherein the amine salt is triethylamine hydrochloride.

4. The process according to claim 1, wherein the aromatic hydrocarbon solvent is toluene or xylene.

* * * * *